United States Patent [19]
Kawamura

[11] Patent Number: 5,706,072
[45] Date of Patent: Jan. 6, 1998

[54] OPHTHALMIC MEASURING APPARATUS

[75] Inventor: Masunori Kawamura, Nagoya, Japan

[73] Assignee: Nidek Company, Ltd., Japan

[21] Appl. No.: 595,827

[22] Filed: Feb. 2, 1996

[30] Foreign Application Priority Data

Feb. 2, 1995 [JP] Japan .................................. 7-039280
Feb. 2, 1995 [JP] Japan .................................. 7-039281

[51] Int. Cl.$^6$ .................................. A61B 3/14; A61B 3/10
[52] U.S. Cl. .................................. 351/209; 351/210; 351/221
[58] Field of Search .................................. 351/211, 212, 351/221, 205, 206, 200, 209, 210, 246, 247

[56] References Cited

U.S. PATENT DOCUMENTS 5,090,799   2/1992   Makino et al. .................................. 351/221

*Primary Examiner*—Hung X. Dang
*Attorney, Agent, or Firm*—Rossi & Associates

[57] ABSTRACT

An ophthalmic measuring apparatus is provided for automatically detecting blinking and insufficient fixation of an eye under examination, and the light reflected from the cornea, as well as for automatically correcting the variation of sensitivity of the apparatus without using any special calibration devices, in order to obtain highly reliable measurements. The apparatus comprising a laser beam projecting optical system for emitting and converging a laser beam to the crystalline lens of the eye and a scattered light detecting optical system for detecting light scattered by the protein molecules within the crystalline lens through a light-receiving optical system into a photoelectric transducer in order to measure the crystalline lens on the basis of the output signals of the photoelectric transducer.

22 Claims, 4 Drawing Sheets

OPHTHALMIC MEASURING APPARATUS

BACKGROUND OF THE INVENTION

1. Field of the Invention

The present invention relates to an ophthalmic measuring apparatus, and more particularly to an ophthalmic measuring apparatus for emitting and converging a laser beam from a laser beam source to the eyeball of an eye, and guiding the light beam scattered by molecules in the crystalline lens through a light-receiving optical system to a photoelectric transducer, in order to measure the crystalline lens in accordance with the output signals of the photoelectric transducer.

2. Description of Related Art

There have been proposed apparatus for achieving early examination of an cataractous eye or measuring such as radius of particles within the crystalline lens by emitting and converging a laser beam to the eyeball of an eye, by guiding the scattered light scattered by molecules in the crystalline lens of the eye through a light-receiving optical system to a photoelectric transducer, and by determining in accordance with the output signals of the photoelectric transducer. With such apparatus, the eye is to be observed through an observation optical system to align with the site of measurement in the crystalline lens, prior to measurement.

However, even when properly aligned, if the subject blinks, or moves eyes, measurement data will be affected. For determining the quality of measurement data by using the apparatus of the prior art, the examiner must observe the condition of the eye under examination.

The method for determine the quality of measurement data by observing the condition of the eye under examination has raised problems of reliability, due to unstable quality or overlooking, since the reference of judgement was totally subjective and differed from an examiner to another.

In practice, a laser beam source or a photoelectric transducer have unavoidably the output variation and the changes in the sensitivity, respectively. In the apparatus of the prior art, in order to correct the results of measurement due to the variation in output from the laser beam source or in sensitivity of the photoelectric transducer, there is adopted a method of correcting for the apparatus by providing a calibration device such as a model-eye with a predetermined reference value, and by comparing the actually measured value of such device with its reference value to determine the correction value.

Since the correction with a calibration device such as a model-eye may be difficult to use readily and frequently, there have been raised problems that the reliability of the measurement data may not be sufficient, if the output from the laser beam source or the sensitivity of the photoelectric transducer varies during the period of time after a calibration and before the next calibration.

SUMMARY OF THE INVENTION

The present invention has been made in view of the above circumstances and is intended to overcome the above problems. It is an object of the present invention to provide an ophthalmic measuring apparatus, which may automatically detect the blink and movement of an eye of the subject under examination and the reflected light from the cornea, to achieve highly reliable results of measurements.

Another object of the present invention is to provide an ophthalmic measuring apparatus, which, with no special calibration devices used, may automatically correct the changes in sensitivity of the apparatus to obtain highly reliable results of measurements.

Additional objects and advantages of the present invention will be set forth in part in the description which follows and in part will be obvious from the description, or may be learned by practice of the present invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic measuring apparatus of this invention comprises a laser beam projecting optical system for emitting and converging a laser beam emitted from a laser beam source to the crystalline lens of an eye, a scattered light detecting optical system including a photoelectric transducer for detecting light scattered by molecules in the crystalline lens from the laser beam, an abnormal measurement detecting optical system for detecting the abnormality of measurement, a determining means for determining the existence or absence of the abnormality of measurement on the basis of the results of detection provided by the abnormal measurement detecting optical system, a detecting means for detecting one of the change in the output from the laser beam source and the sensitivity of the photoelectric transducer, and an arithmetic means for correcting the results of the measurement in accordance with the results of the detection from the detecting means.

Another aspect of this invention comprises a laser beam projecting optical system for emitting and converging a laser beam emitted from a laser beam source to the crystalline lens of an eye, a scattered light detecting optical system including a photoelectric transducer for detecting light scattered by molecules in the crystalline lens from the laser beam, an abnormal measurement detecting optical system for detecting the abnormality of measurement, a determining means for determining the existence or absence of the abnormality of measurement on the basis of the results of detection provided by the abnormal measurement detecting optical system, a guide optical system for directly guiding the laser beam emitted from the laser beam source to the surface of the photoreceptor of the photoelectric transducer, a selecting means for selecting the laser beam incident onto the photoelectric transducer among the one through the guide optical system or the one through the scattered light detecting optical system, and an arithmetic means for detecting the amount of the incident light through the guide optical system to the photoelectric transducer to correct the measured value on the basis of the detected amount.

The abnormal measurement detecting optical system is in common with the scattered light detecting optical system.

The determining means comprises an extracting means for extracting the variation of the light intensity detected by the abnormal measurement detecting optical system, a storing means for storing the variation of the light intensity extracted by the extracting means, and a comparing means for comparing the light intensity stored in the storing means with a predetermined reference of the light intensity.

The predetermined reference of the light intensity which is used in the comparing means comprises preselected threshold values for its upper limit and lower limit.

The guide optical system comprises a diffuser and optical fibers to introduce a diffused laser beam.

The selecting means is provided with a first shutter along with the optical path of the scattered light detecting optical system, and further comprises a control means which closes the first shutter for correction.

The selecting means is provided with a first shutter along with the optical path of the scattered light detecting optical system, and a second shutter along with the optical path of the guide optical system, and further comprises a control means which controls the motion of the first and second shutters.

The selecting means is controlled such that the laser beam through the guide optical system is incident onto the photoelectric transducer at least once per measurement.

The apparatus further comprises a notifying means for reporting the results of the determination by the determining means.

According to the present invention, it is capable of preventing erroneous measurement results from accepting by automatically detecting errors due to, for example, blinking or moving eye of the subject under examination, and the reflection from the associated cornea.

Also, the ophthalmic measuring apparatus of the present invention is capable of preventing the measurement results from varying due to changes in, for example, sensitivity of the apparatus, with no special calibration devices provided, and obtaining accurate results of measurements by incorporating the execution of calibration of measurement results into the measuring protocol.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Preferred embodiments of the present invention will now be given with reference to the accompanying drawings.

Figure 1:
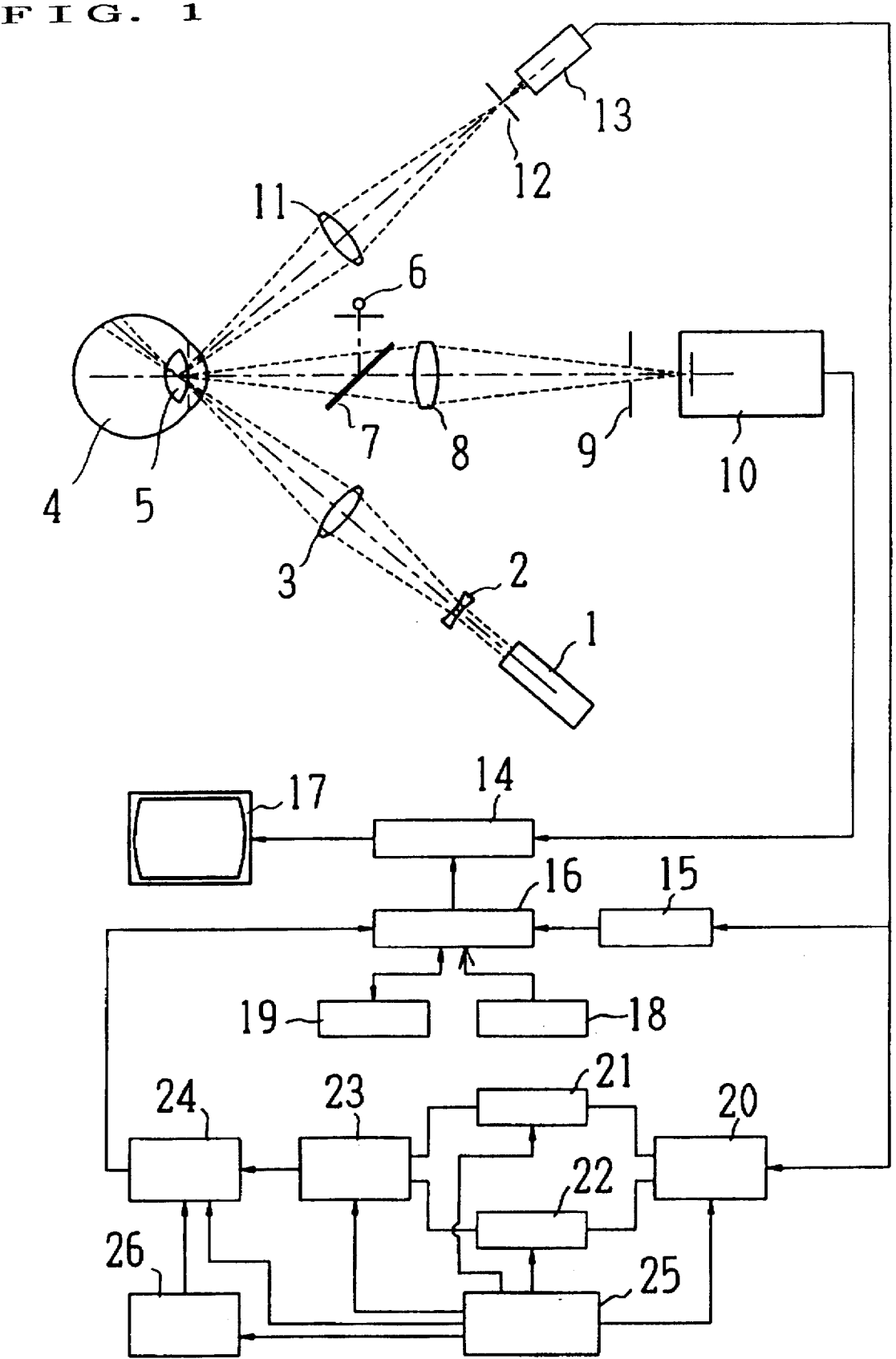
FIG. 1 is a schematic view showing the overview of a first embodiment of an apparatus according to the present invention.

Now referring to FIG. 1, there is shown the overview of an optical system and an electrical system of a measuring apparatus of the first preferred embodiment according to the present invention for measuring protein composition within a crystalline lens.

[Optical System]

In the drawings, reference numeral 1 designates an He—Ne laser beam source for emitting a laser beam to a crystalline lens, 2 is an expander lens, 3 is a condenser lens. The above mentioned members 1 to 3 constitute a laser beam projecting optical system for measuring the protein composition within a crystalline lens. Reference numeral 4 designates an eye under examination, 5 a crystalline lens.

Reference numeral 6 designates a point light source for fixation, and 7 designates a beam splitter. The members 6 and 7 constitute a fixation point projection optical system for projecting a fixation target point into the fundus oculi of the eye.

Reference numeral 8 is an image forming lens, 9 is a diaphragm, and 10 is a CCD camera. The members 8 to 10 constitute an observation optical system for observing the anterior portion of the eye.

Reference numeral 11 is an image forming lens, 12 is an aperture, and 13 is a photoelectric transducer. The members 11 to 13 constitute a scattered light receiving (detecting) optical system.

[Electrical System]

Reference numeral 14 designates an image synthesizing circuit, 15 is an arithmetic circuit for operating on the protein composition within a crystalline lens in response to the output signals of the photoelectric transducer, 16 is a control computer, 17 is a monitor display, 18 is an input switch, and 19 is a storage device.

Reference numeral 20 is a signal switching circuit for input, 21 and 22 are counters, 23 is a signal switching circuit for output, 24 is a memory, 26 is an address generator, 25 is a timing signal generator. The timing signal generator 25 generates control signals for the signal switching circuits 20 and 23, a clear signal for counters 21 and 22, a clock signal for the address generator 26, and a timing signal for writing signals to the memory 24. The members 20 to 26 constitute a sampling system.

The operation of the apparatus with the above mentioned configuration will now be described.

The light emitted from the point light source 6 passes through the beam splitter 7 to the fundus oculi of the eye, then the point light source 6 is used for the eye to be measured as a fixation lamp to fix.

The anterior portion of the eye is illuminated by an illumination light source (not shown), its image is received onto the CCD camera 10 by passing through the image forming lens 8 of the observation optical system, and the diaphragm 9, to be displayed on the monitor display 17. The laser beam output from the laser beam source 1 is expanded its bundle by the expander lens 2, then converged by the condenser lens 3 to be irradiated from an oblique direction to the crystalline lens 5 of the eye.

The examiner then decides the site to measure, while observing the image of the anterior portion of the eye displayed on the monitor display 17, and the converged laser beam passing through the crystalline lens 5.

Once the site to measure decided, the actual measurement can be started by pressing a start button provided in the input switch 18. The laser beam, irradiated to the crystalline lens 5 of the eye 4, is scattered by the protein molecules in the crystalline lens 5. The scattered light is gathered by the image forming lens 11 to the aperture 12 and introduced into the photoelectric transducer 13.

The photoelectric transducer 13 outputs an electric signal corresponding to the intensity of the scattered light incident thereon, which signal is transmitted to the arithmetic circuit 15. The arithmetic circuit 15 determines a correlation function of the fluctuation with time of the intensity of the scattered light. Based on this correlation function, the control computer 16, in turn, can derive the results on the protein composition in the crystalline lens. In the measurement, as described for example, in the Japanese Patent Laid-open No. Hei 6-505650 (PCT No. wo 92/11799)

entitled as "Method of Detecting Cataract and Apparatus for Carrying out the Same," the correlation function of the fluctuation with time of the intensity of the scattered light may be given by the following expression:

$$C(\tau)=\alpha(I_f e^{-\tau/\tau_f}+I_s \cdot e^{-\tau/\tau_s})^2+(I_f+I_s+I_{imm})^2$$

where:
- τf: Constant relating to the size of not agglutinated particles
- τs: Constant relating to the size of agglutinated particles
- If: Intensity of light scattered by not agglutinated particles
- Is: Intensity of light scattered by agglutinated particles
- Iimm: Intensity of light scattered by stationary particles
- α: Constant specific to the optical system.

The protein composition of the crystalline lens is calculated from the ratio (quantity) between the intensity If of light scattered by not agglutinated particles and the intensity Is of light scattered by agglutinated particles.

The signal output from the photoelectric transducer 13 is passed through the signal switching circuit 20 and counted alternately at the counters 21 and 22, for each of predefined sampling period regulated by the timing signal generator 25. During the sampling period which is counted by the counter 21, the output from the counter 22 is connected through the signal switching circuit 23 to the memory 24, then the contents of the counter 22 is written to the address generated by the address generator 26. Thereafter the counter 22 will be cleared.

During the succeeding sampling period, the signal output from the photoelectric transducer 13 is passed through the signal switching circuit 20 and counted by the counter 22. The contents of the counter 21 is then written through the signal switching circuit 23 to the next address in the memory 24, the counter 21 will be cleared thereafter. By repeating this, the signal output from the photoelectric transducer 13 will be stored in the memory 24 in a continuous manner for each sampling period.

Figure 2:
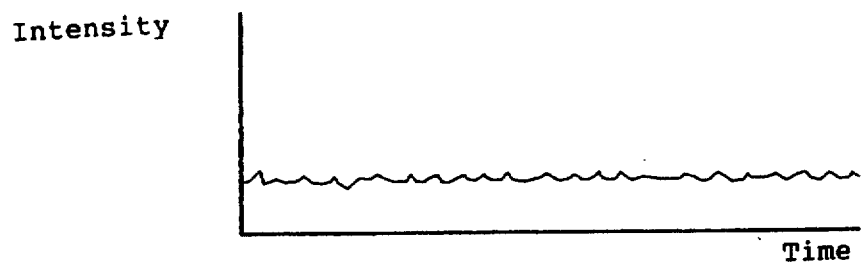
FIG. 2(a) is a chart showing an example of sampling data associated with a proper measurement.
FIG. 2(b) is a chart showing an example of sampling data associated with a measurement when the eye under examination blinks.
FIG. 2(c) is a chart showing an example of sampling data associated with a measurement with reflected light from the cornea being received.
Figure 2:
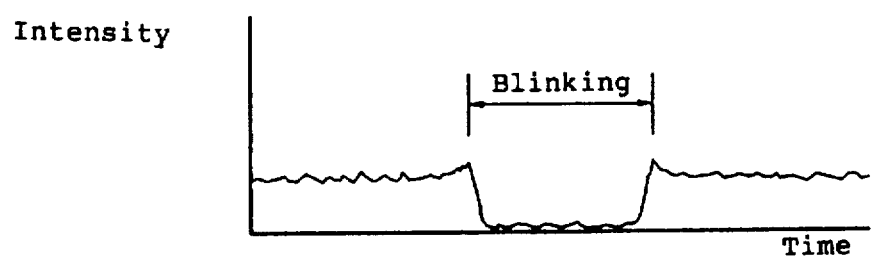
Figure 2:
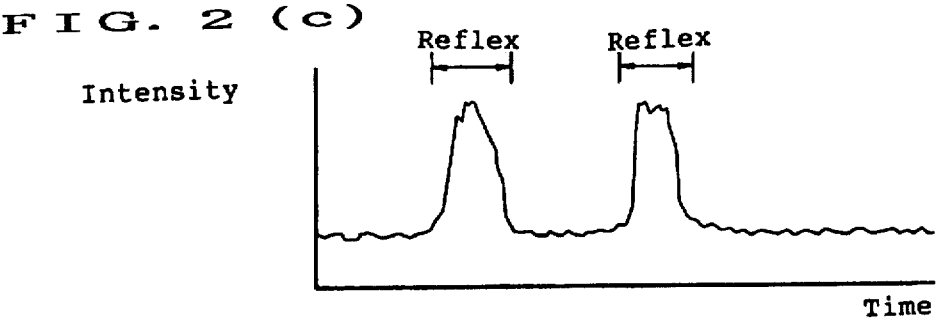

Referring now to FIG. 2, which shows graphically the changes in the sampling data stored in the memory 24. The abscissa indicates the number of sampling period (time). The ordinate indicates the counted value at the counter either 21 or 22.

FIG. 2(a) depicts an example of output when measured normally. FIG. 2(b) depicts an example of output in which the eye under examination suddenly blinked during measurement. In the period during which the eye under examination is closed, the intensity of the scattered light is extremely decreased because the scattered light scattered by the protein molecules in the crystalline lens 5 was not received.

FIG. 2(c) depicts another example of output when the light reflected from the cornea was received during measurement. In the period during which the reflected light from the cornea was received, the intensity of the light is extremely increased because the intensity of the reflected light is much greater than the intensity of the scattered light from the protein molecules in the crystalline lens 5.

Figure 3:
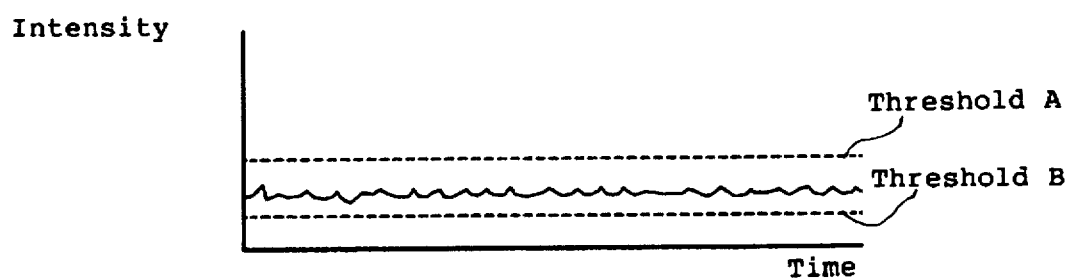
FIG. 3 is an example with a threshold value applied to the measured sampling data.

The control computer 16 determines the quality of the results of measurement obtained through the arithmetic circuit 15, on the basis of the light intensity signal stored in the memory 24. In this determination process, for example, by presetting a threshold value A at the level of the upper limit and another threshold value B at the level of the lower limit, as shown in FIG. 3, the quality of the results may be determined from the absence or presence of an abnormal signal outside of the range defined by these two threshold values.

The control computer 16 may display an error message on the monitor display 17 through the image synthesizing circuit 14 for request the examiner to measure again, if there has been detected an abnormal signal which falls outside the range defined by the threshold values. It may be presumably appreciated that by estimating the cause of anomaly from the type of the abnormal signal, additional information such as "blink during measurement" is displayed with the error message. In the case in which there has been no abnormal signals outside the range defined by the threshold values, the computed results from the aforementioned arithmetic circuit 15 is processed in a predetermined manner to calculate the results of measurement, then the results of measurement will be displayed on the monitor display 17 as well as stored in the storage device 19.

Figure 4:
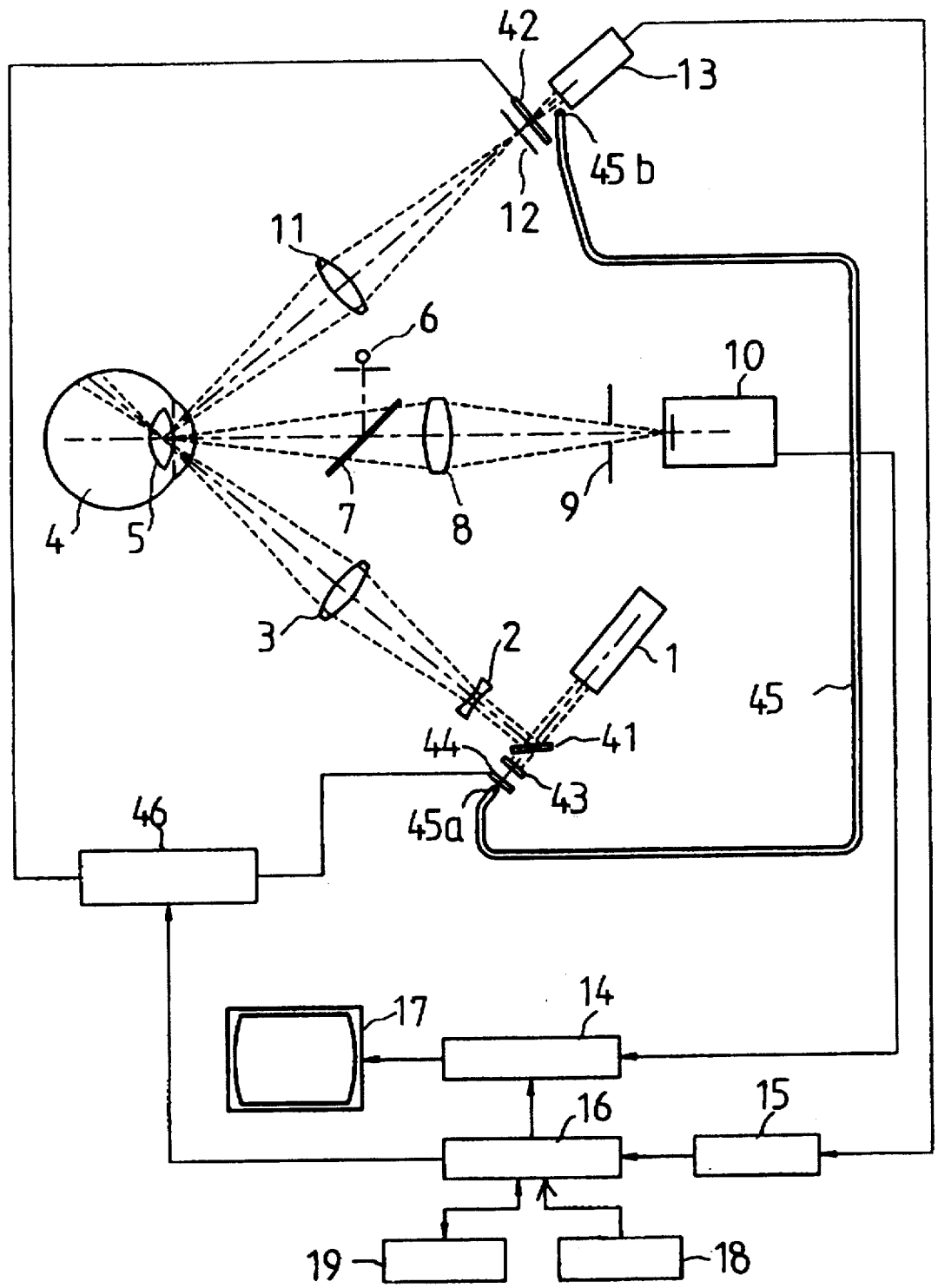
FIG. 4 is a schematic view showing the overview of a second embodiment of the apparatus according to the present invention.

Now referring to FIG. 4 in which the overview of an apparatus of the second embodiment, for measuring the protein composition in a crystalline lens, according to the present invention. In FIG. 4 as like numerals referring to like parts for the configuration of the above mentioned first preferred embodiment of the present invention, description of the components in details will be omitted.

Reference numeral 41 designates a beam splitter located in the laser projecting optical system, 42 and 44 are shutters, 43 is a diffuser, and 45 is a bundle of fiber optics. The beam splitter 41, and shutter 42, 44, and diffuser 43 as well as components through optical fibers 45 constitute a calibration optical system for calibrating the apparatus. Reference numeral 46 designates a shutter driver.

The operation of the apparatus with the above mentioned configuration will now be described.

At first, the calibration of the apparatus for the variation in output of the laser beam source and in sensitivity of the photoelectric transducer will be explained. For calibration, the control computer 16 makes the shutter driver 46 active to close the shutter 42 and open the shutter 44. The laser beam output from the laser beam source 1 is passed through the beam splitter 41 and diffused by the diffuser 43. Part of the diffused light passes through the opened shutter 44, enters to the optical fibers 45 from one of their ends 45a, exits from another end 45b of the optical fibers 45 and then enters directly to the photoelectric transducer 13. At this time as the shutter 42 is closed, only part of the laser beam emitted from the laser beam source 1 is entered directly to the photoelectric transducer 13.

On the output signal of the photoelectric transducer 13, the arithmetic circuit 15 operates in a predetermined manner, so that the control computer 16 may be obtained a calibrating value with the variance in output of the laser beam source 1 and the variance in sensitivity of the photoelectric transducer 13. By comparing this calibrating value with the reference value predefined in the factory, the results of measurement will be corrected.

Assuming that the obtained calibrating value C, the reference value predefined in the factory S, and the results before correction D, the results of measurement after correction D' will be given by:

D'=D*S/C.

Figure 5:
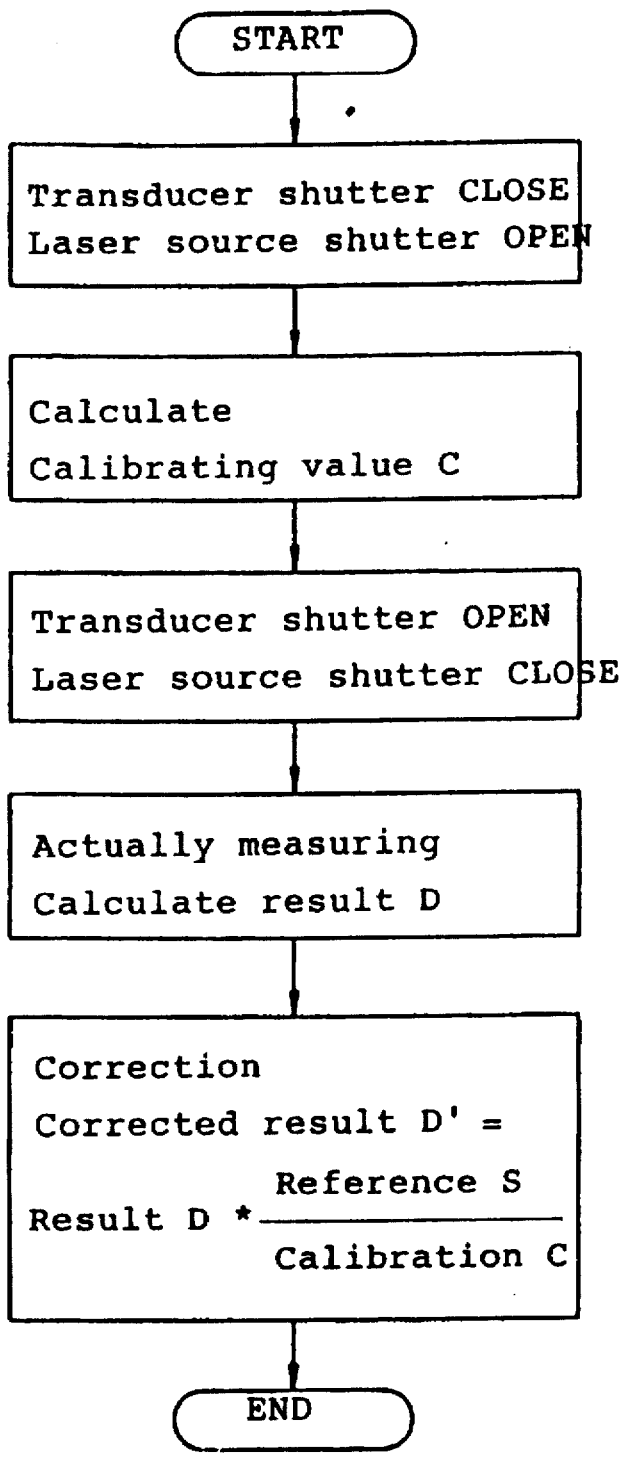
FIG. 5 is a flowchart explaining the function of the apparatus of another embodiment in which calibration is made for each measurement.

Referring to the flowchart depicted in FIG. 5, the operation of an apparatus of the preferred embodiment in which the calibration will be done for each measurement will be describe hereinunder.

The examiner instructs the subject to fix an eye under examination onto the point light source 6 as a fixation lamp. Then by observing the anterior portion of the eye on the monitor display 17, verifying the location of the light beam from the laser beam source 1 and manipulating a joystick mechanism to decide the site of measurement. Input to the input switch 18 causes a trigger signal to be sent, and the measurement to be started.

The laser beam emitted from the laser beam source 1 is split by the beam splitter 41 into the laser beam for use in measurement and the laser beam for use in calibration of the apparatus.

The control computer 16 drives the shutter driver 46 to close the shutter 42 and open the shutter 44 so as to obtain the above mentioned calibrating value C from the output signal of the photoelectric transducer 13. Once obtained the calibrating value C, the control computer 16 temporarily stores that value in the memory in its circuit.

Then the control computer 16 drives the shutter driver 46 to open the shutter 42 and close the shutter 44. The laser beam reflected by the beam splitter 41 is expanded its bundle by the expander lens 2, then converged by the condenser lens 3 to be irradiated from an oblique direction to the crystalline lens 5 of the eye 4. The laser beam, irradiated to the crystalline lens 5 of the eye 4, will be scattered by the protein molecules in the crystalline lens 5. The scattered light is gathered by the image forming lens 11 to be focused on the position of the aperture 12, then passed through the aperture 12 and the enter to shutter 42 to enter to the photoelectric transducer 13.

The photoelectric transducer 13, as described above with reference to the first embodiment, outputs an electric signal corresponding to the intensity of the incident scattered light, which signal, in turn, is inputted to the arithmetic circuit 15. The arithmetic circuit 15 determines, based on the inputted signal, a correlation function of the fluctuation with time of the intensity of the scattered light. Based on this correlation function, the control computer 16, in turn, can derive the results D of the information on the scattered light from the protein composition in the crystalline lens. In the measurement, according to the formula described hereinabove with reference to the first embodiment, the protein composition within a crystalline lens may be computed.

The computer 16 calculates the corrected results of measurement D' according to the formula of correction hereinabove (D'=D*S/C), to display that results on the monitor display 17 through the image synthesizing circuit 14. The corrected results are also stored in the memory 19.

As can be seen, the apparatus detects the variation of output of the laser beam source 1 and the variation of sensitivity of the photoelectric transducer 13 for each measurement, and it derives the results of measurement after respective correction.

The present invention may be embodied in other specific forms without departing from the spirit or essential characteristics thereof. For instance, although in the first embodiment, the optical system for detecting abnormal measurement shares components with the optical system for measuring, respective systems may be constituted of their proprietary components.

Also, in the second embodiment, the calibration of the output of the laser beam source 1 and that of the sensitivity of the photoelectric transducer 13 may be independently provided. More specifically, by splitting further the light path split by the beam splitter 41 by using another splitter to locate an anterior photoelectric transducer on one of paths to directly detect the output of the laser beam source 1, the variation of sensitivity of the photoelectric transducer 13 may be calculated by directly comparing the detected output of the laser beam source 1 with the amount of light received by the photoelectric transducer 13.

In addition, in the case in which the variation of either the output from the laser beam source 1 or the sensitivity of the photoelectric transducer 13 exceeds a predetermined range, a request for their replacement may be displayed.

The forgoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the present invention and its practical application to enable one skilled in the art to utilize the present invention in various embodiments and with various modifications as are suited to the particular use contemplated. It is intended that the scope of the present invention be defined by the claims appended hereto, and their equivalents.

What is claimed is:

1. An ophthalmic measuring apparatus comprising:

a laser beam projecting optical system for emitting and converging a laser beam emitted from a laser beam source to the crystalline lens of an eye;

a scattered light detecting optical system including a photoelectric transducer for detecting light scattered by molecules in the crystalline lens from the laser beam;

an abnormal measurement detecting optical system for detecting the abnormality of measurement;

a determining means for determining the existence or absence of the abnormality of measurement on the basis of the results of detection provided by said abnormal measurement detecting optical system;

a detecting means for detecting one of the change in the output from said laser beam source and the sensitivity of said photoelectric transducer; and an arithmetic means for correcting the results of the measurement in accordance with the results of the detection from said detecting means.

2. An ophthalmic measuring apparatus according to claim 1, wherein the abnormal measurement detecting optical system is in common with said scattered light detecting optical system.

3. An ophthalmic measuring apparatus according to claim 1, wherein said determining means comprises:

an extracting means for extracting the variation of the light intensity detected by said abnormal measurement detecting optical system;

a storing means for storing the variation of the light intensity extracted by said extracting means; and a comparing means for comparing the light intensity stored in said storing means with a predetermined reference of the light intensity.

4. An ophthalmic measuring apparatus according to claim 3, wherein said predetermined reference of the light intensity which is used in the comparing means comprises preselected threshold values for its upper limit and lower limit.

5. An ophthalmic measuring apparatus comprising:

a laser beam projecting optical system for emitting and converging a laser beam emitted from a laser beam source to the crystalline lens of an eye;

a scattered light detecting optical system including a photoelectric transducer for detecting light scattered by molecules in the crystalline lens from said laser beam;

an abnormal measurement detecting optical system for detecting the abnormality of measurement;

a determining means for determining the existence or absence of the abnormality of measurement on the basis of the results of detection provided by said abnormal measurement detecting optical system;

a guide optical system for directly guiding the laser beam emitted from said laser beam source to the surface of the photoreceptor of said photoelectric transducer;

a selecting means for selecting the laser beam incident onto said photoelectric transducer among the one through said guide optical system or the one through said scattered light detecting optical system; and an arithmetic means for detecting the amount of the incident light through said guide optical system to said photoelectric transducer to correct the measured value on the basis of the detected amount.

6. An ophthalmic measuring apparatus according to claim 5, wherein the abnormal measurement detecting optical system is in common with said scattered light detecting optical system.

7. An ophthalmic measuring apparatus according to claim 5, wherein said determining means comprises:

an extracting means for extracting the variation of the light intensity detected by said abnormal measurement detecting optical system;

a storing means for storing the variation of the light intensity extracted by said extracting means; and a comparing means for comparing the light intensity stored in said storing means with a predetermined reference of the light intensity.

8. An ophthalmic measuring apparatus according to claim 7, wherein said predetermined reference of the light intensity which is used in the comparing means comprises preselected threshold values for its upper limit and lower limit.

9. An ophthalmic measuring apparatus according to claim 5, wherein said guide optical system comprises a diffuser and optical fibers to introduce a diffused laser beam.

10. An ophthalmic measuring apparatus according to claim 5, wherein said selecting means is provided with a first shutter along with the optical path of said scattered light detecting optical system, and further comprises a control means which closes said first shutter for correction.

11. An ophthalmic measuring apparatus according to claim 5, wherein said selecting means is provided with a first shutter along with the optical path of said scattered light detecting optical system, and a second shutter along with the optical path of said guide optical system, and further comprises a control means which controls the motion of said first and second shutters.

12. An ophthalmic measuring apparatus according to claim 5, wherein said selecting means is controlled such that the laser beam through the guide optical system is incident onto said photoelectric transducer at least once per measurement.

13. An ophthalmic measuring apparatus for detecting the eye under an examination comprising:

a laser beam projecting optical system for emitting and converging a laser beam emitted from a laser beam source to an eye;

a scattered light detecting optical system for detecting light scattered by molecules in the eye composition from said laser beam;

a determining means for determining the existence or absence of the abnormality of measurement on the basis of the results of the detection provided by said scattered light detecting optical system; and a notifying means for reporting the results of the determination by said determining means.

14. An ophthalmic measuring apparatus according to claim 13, wherein said laser beam projecting optical system converges the laser beam within the crystalline lens of the eye.

15. An ophthalmic measuring apparatus according to claim 13, wherein said determining means comprises:

an extracting means for extracting the variation of the light intensity detected by said abnormal measurement detecting optical system;

a storing means for storing the variation of the light intensity extracted by said extracting means; and a comparing means for comparing the light intensity stored in said storing means with a predetermined reference of the light intensity.

16. An ophthalmic measuring apparatus according to claim 15, wherein said predetermined reference of the light intensity which is used in the comparing means comprises preselected threshold values for its upper limit and lower limit.

17. An ophthalmic measuring apparatus comprising a laser beam projecting optical system for emitting and converging a laser beam emitted from a laser beam source to the eyeball of an eye, and a scattered light detecting optical system including a photoelectric transducer for detecting light scattered by molecules in the crystalline lens from said laser beam, for measuring the characteristics of the tissue of the crystalline lens in accordance with the light intensity detected by said photoelectric transducer, said apparatus comprising:

a detecting means for detecting either one of the variation in the output of said laser beam source and the sensitivity of said photoelectric transducer; and an arithmetic means for correcting the results of measurement in accordance with the results of the detection from said detecting means.

18. An ophthalmic measuring apparatus comprising a laser beam projecting optical system for emitting and converging a laser beam emitted from a laser beam source to the eyeball of an eye, and a scattered light detecting optical system including a photoelectric transducer for detecting light scattered by molecules in the crystalline lens from said laser beam, for measuring the characteristics of the tissue of the crystalline lens in accordance with the light intensity detected by said photoelectric transducer, said apparatus comprising:

a guide optical system for directly guiding the laser beam emitted from said laser beam source to the surface of the photoreceptor of said photoelectric transducer;

a selecting means for selecting the laser beam incident into said photoelectric transducer among the one through said guide optical system or the one through said scattered light detecting optical system; and an arithmetic means for detecting the amount of the incident light through said guide optical system to said photoelectric transducer to correct for the measured value on the basis of the detected amount.

19. An ophthalmic measuring apparatus according to claim 18, wherein said guide optical system comprises a diffuser and optical fibers to introduce a diffused laser beam.

20. An ophthalmic measuring apparatus according to claim 18, wherein said selecting means is provided with a first shutter along with the optical path of said scattered light detecting optical system, and further comprises a control means which closes said first shutter for correction.

21. An ophthalmic measuring apparatus according to claim 18, wherein said selecting means is provided with a first shutter along with the optical path of said scattered light detecting optical system, and a second shutter along with the optical path of said guide optical system, respectively, and further comprises a control means which controls the motion of said first and second shutters.

22. An ophthalmic measuring apparatus according to claim 18, wherein said selecting means is controlled such that the laser beam through the guide optical system is incident to said photoelectric transducer at least once per measurement.

* * * * *